(12) United States Patent
Sisbot

(10) Patent No.: US 9,348,336 B2
(45) Date of Patent: May 24, 2016

(54) ROBOT ASSISTANCE FOR DETECTING, MANAGING, AND MITIGATING RISK

(71) Applicant: TOYOTA JIDOSHA KABUSHIKI KAISHA, Toyota-shi, Aichi-ken (JP)

(72) Inventor: Emrah Akin Sisbot, Mountain View, CA (US)

( * ) Notice: Subject to any disclaimer, the term of this patent is extended or adjusted under 35 U.S.C. 154(b) by 0 days.

(21) Appl. No.: 14/485,544

(22) Filed: Sep. 12, 2014

(65) Prior Publication Data

US 2016/0077526 A1    Mar. 17, 2016

(51) Int. Cl.
*A61H 3/06* (2006.01)
*G05D 1/02* (2006.01)
*H04L 29/08* (2006.01)

(52) U.S. Cl.
CPC .............. *G05D 1/0214* (2013.01); *H04L 67/10* (2013.01); *Y10S 901/01* (2013.01)

(58) Field of Classification Search
CPC ...... B25J 9/1689; B25J 9/1679; B25J 9/1674; B25J 9/1697; B25J 11/008; B25J 11/009; A61H 3/06; A61H 3/061; A61H 3/068
USPC .................. 700/245, 253, 257, 258, 259, 264
See application file for complete search history.

(56) References Cited

U.S. PATENT DOCUMENTS

| | | | | |
|---|---|---|---|---|
| 5,687,136 A | * | 11/1997 | Borenstein | A61H 3/061 367/116 |
| 2008/0198222 A1 | * | 8/2008 | Gowda | A61H 3/061 348/62 |
| 2009/0326713 A1 | * | 12/2009 | Moriya | A63H 17/00 700/255 |
| 2010/0063627 A1 | * | 3/2010 | Kitahama | A61H 3/061 700/253 |

OTHER PUBLICATIONS

Kulyukin, V., Gharpure, C., Sute, P., De Graw, N., & Nicholson, J. (2004) A obotic wayfinding system for the visually impaired. Proceedings of the 16th conference on Innovative applications of artificial intelligence, 864-869.
Shen, D. F., Kil, S. K., Jang, T. J., Lee, E. H., & Hong, S. H. (2004) A Study on Path Guidance System of Guide Robot for Visually Impaired. ISARC 2004 21st International Symposium on Automation and Robotics in Construction, 5 pgs.
Lacey, G. & MacNamara, S. (2000) Context-Aware Shared Control of a Robot Mobility Aid for the Elderly Blind, International Journal of Robotics Research, 1054-1065.

* cited by examiner

*Primary Examiner* — Stephen Holwerda
(74) *Attorney, Agent, or Firm* — Burbage Law, P.C.; Jon Burbage; Elizabeth Ruzich

(57) ABSTRACT

The disclosure includes a system and method for using a robot to prevent risk to a user by identifying a point of interest, determining whether the point of interest is a risk for the user with visual impairments based on the user's position, responsive to a first predetermined threshold for distance being met, determining where to move the robot to mitigate the risk to the user, and instructing the robot to move to a new location. The robot may move between the user and the point of interest to prevent the user from colliding with the point of interest. The robot may use an auditory or tactile warning to warn the user. The tactile warning may be transmitted to a walking stick or a belt worn by the user.

21 Claims, 5 Drawing Sheets

ROBOT ASSISTANCE FOR DETECTING, MANAGING, AND MITIGATING RISK

BACKGROUND

The specification relates to using a robot to prevent risk to a user.

Travelling can be difficult for people with visual impairment because they may not be aware of dangerous or uncomfortable situations that are near them. Drops, objects, and obstacles pose a threat to the blind person's safety. Although a guidance system might consider these dangers, there is no guarantee that the guided person will follow the guidance closely enough. Any deviations from the guided path might be a potential danger. In addition, the dangers may change, such as when a visually impaired user tries to move near sighted people because they can move in a very dynamic fashion. In the presence of a crowd the blind person could feel uncomfortable of the many people quickly passing nearby.

Existing solutions involve a blind person holding a robot with one or two hands. The robot moves towards a direction and the person follows it. Since the robot is between the user and the environment, in case of a danger such as a crowd the robot receives the first impact, thus saving the user from dangers directly in front of the user. However, the robot does nothing to protect the user against dangers or uncomfortable situations that can appear from other directions.

SUMMARY

According to one innovative aspect of the subject matter described in this disclosure, a system for preventing risk to a user is described. The system includes a processor and a memory storing instructions that, when executed, cause the system to: identify a point of interest, determine whether the point of interest is a risk for a user with visual impairments based on the user's position, responsive to a first predetermined threshold for distance being met, determine where to move a robot to mitigate the risk to the user, and instruct the robot to move to a new location.

In general, another innovative aspect of the subject matter described in this disclosure may be embodied in methods that include monitoring, with one or more processors, for a risky situation, identifying a point of interest, determining whether the point of interest is a risk for a user with visual impairments based on the user's position, responsive to a first predetermined threshold for distance being met, determining where to move a robot to mitigate the risk to the user, and instructing the robot to move to a new location.

Other aspects include corresponding methods, systems, apparatus, and computer program products for these and other innovative aspects.

These and other embodiments may each optionally include one or more of the following operations and features. For instance, the operations include: estimating a degree of risk based on risk factors by assigning a score to the point of interest based on a path associated with the user; determining whether to warn the user and responsive to determining to warn the user, providing a warning to the user; determining whether to warn the user and responsive to determining not to warn the user, identifying a point of interest; responsive to a second predetermined threshold for confidence being met, determining where to move the robot to mitigate risk to the user; and responsive to a second predetermined threshold for confidence failing to be met, identifying a point of interest. For instance, the features include the warning being at least one of an auditory warning and a tactile warning; the warning being a tactile warning and further comprising transmitting the warning to a walking stick that provides the user with haptic feedback; and the point of interest comprising at least one of a drop, a fixed obstacle, and a mobile object.

Throughout the disclosure, the term "data" may be used to represent any digital data undergoing the transfer functions or operations described herein. The digital data may include, but is not limited to, network services data, connectivity map data, journey data, user profile data, time synchronicity data, historical journey data, preference hierarchy data, dead zone data, navigation map data, mesh network data, velocity data, data to be shared between two or more entities (e.g., servers, vehicle systems, mobile client devices, client devices, etc.), and data to be transferred between two or more entities.

The disclosure is particularly advantageous in a number of respects. For example, the robot can be placed in strategic locations to ensure the user's safety and comfort from directions other than directly in front of the user. As a result, vision-impaired users can live more mobile and active lifestyles with decreased risk of injury.

The advantages of the system described herein are provided by way of example, and the system may have numerous other advantages.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

System Overview

Figure 1:
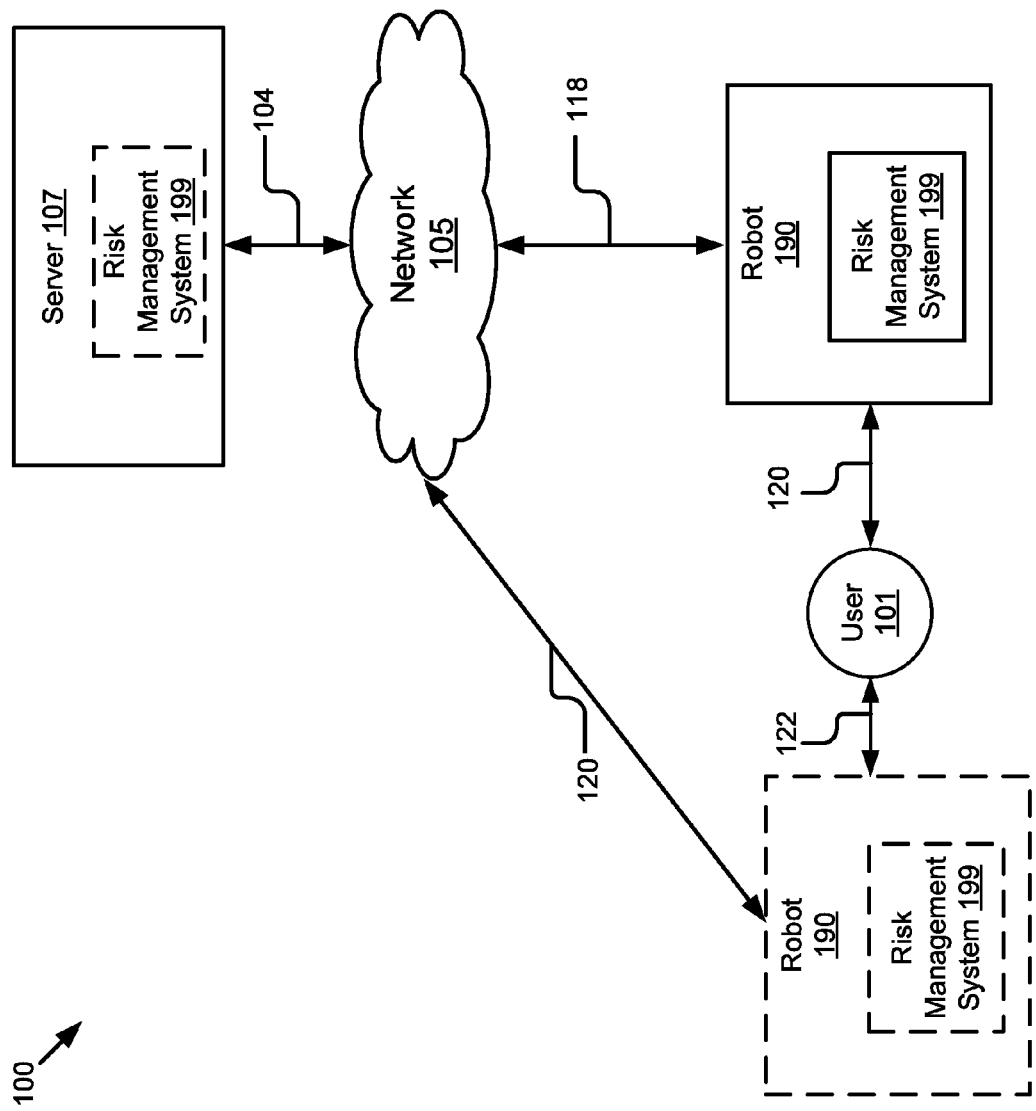
FIG. 1 is a block diagram illustrating an example system for using a robot to prevent risk to a user.

FIG. 1 illustrates a block diagram of some embodiments of a system 100 for using a robot to prevent risk to a user. The system 100 includes a server 107 communicatively coupled to a network 105 via signal line 104, a robot 190 communicatively coupled to the network 105 via signal line 118, and another optional robot 190 communicatively coupled to the network 105 via signal line 120. A user 101 is communicatively coupled to the robot(s) 190 via signal line 120 and optionally signal line 122.

While FIG. 1 illustrates one user 101 and one server 107, the disclosure applies to a system architecture including one or more users 101 and one or more servers 107. Furthermore, although FIG. 1 illustrates one network 105 coupled to the entities of the system 100, in practice one or more networks 105 of various types may be connected to these entities.

The network 105 can be a conventional type, wired or wireless, and may have numerous different configurations including a star configuration, token ring configuration, or other configurations. Furthermore, the network 105 may include a local area network (LAN), a wide area network (WAN) (e.g., the Internet), or other interconnected data paths across which multiple devices may communicate. In some embodiments, the network 105 may be a peer-to-peer network. The network 105 may also be coupled to or includes portions of a telecommunications network for sending data in a variety of different communication protocols. In some embodiments, the network 105 includes Bluetooth® communication networks or a cellular communications network for sending and receiving data including via short messaging service (SMS), multimedia messaging service (MMS), hypertext transfer protocol (HTTP), direct data connection, WAP, e-mail, etc. In some embodiments, the network 105 may include a GPS satellite for providing GPS navigation to the robot 190. The network 105 may be a mobile data network, for example, 3G, 4G, LTE, Voice-over-LTE ("VoLTE"), or any other mobile data network or combination of mobile data networks. In some embodiments, the network 105 may be a combination of different networks.

The robot 190 may be a computing device that includes a memory and a processor, for example, a laptop computer, a desktop computer, a tablet computer, a mobile telephone, a personal digital assistant ("PDA"), a mobile e-mail device, a portable game player, a portable music player, a connected device or wearable computer (e.g., a smart watch, smart glasses, fitness tracker, etc.), a television with one or more processors embedded therein or coupled thereto, a vehicle, or other electronic device capable of accessing the network 105. The robot 190 includes a risk management system 199. The risk management system 199 warns a user 101 of certain risks. The user 101 may interact with the robot 190 via auditory or haptic notifications. For example, where the user 101 is too close to a risk, the risk management system 199 instructs the robot 190 to warn the user 101 to change directions. In another example, the robot 190 may use haptic feedback by vibrating in a direction that the user 101 should move. Multiple robots 190 may be used to warn the user 101 of risks that come from multiple directions at the same time. The second robot 190 is depicted with dashes to indicate that multiple robots are optional.

The robot 190 may include functionality to enable a user to consume network services. The network services may include any service accessible via the network 105. For example, the network services include navigation instructions, streaming audio or video (such as Pandora™, Spotify™, iTunes™, Google Play™, YouTube™, etc.), social networking (such as Facebook™, Google+™, LinkedIn™, Tinder™, QQ™, etc.), microblogging (such as Twitter™, Tumblr™, etc.), online chatting (such as SnapChat™, WhatsApp™, etc.), online content sharing (such as Instagram™, Pinterest™, etc.), email (such as Gmail™, Outlook™, Yahoo! Mail™, etc.), file sharing (such as DropBox™, Google Drive™, MS One Drive™, Evernote™, etc.), calendar and scheduling (such as Google™ Calendar, MS Outlook™, etc.), etc.

In some embodiments, the risk management system 199 is also stored on a server 107. The risk management system 199 is depicted with dashed lines in FIG. 1 in order to indicate that the risk management system 199 is optionally stored on the server 107. The server 107 includes a memory and a processor. In one embodiment, the risk management system 199 is stored in part on the robot 190 and in part on the server 107. For example, the robot 190 transmits information about risks to the server 107, which determines whether the risks exceed a threshold and, as a result, whether the user 101 should be notified. The server 107 may transmit the determination to the robot 190, which notifies the user.

The risk management system 199 may include code and routines for using the robot to prevent risk to a visually impaired user, for example, a blind user. The risk management system 199 identifies a point of interest, such as a drop, a fixed obstacle, or a mobile object. The risk management system 199 determines whether the point of interest is a risk for the user based on the user's position. The risk management system 199 estimates the degree of risk based on distance and confidence. If a first predetermined threshold for distance and a second predetermined threshold for confidence are met, the risk management system 199 determines where to move the robot 190 to mitigate risk to the user. In some embodiments, the risk management system 199 also instructs the robot 190 to provide a warning to the user, such as an auditory warning or a tactile warning in the form of vibrations. In some embodiments, the risk management system 199 transmits an instruction to another device to provide the alert. For example, the risk management system 199 transmits a haptic alert to a walking stick or a belt that is configured to vibrate in different directions to guide the user away from the risk.

In some embodiments, the risk management system 199 can be implemented using hardware including a field-programmable gate array ("FPGA") or an application-specific integrated circuit ("ASIC"). In some other embodiments, the risk management system 199 can be implemented using a combination of hardware and software. The risk management system 199 may be stored in a combination of the devices and servers, or in one of the devices or servers.

Example Risk Management System

Figure 2:
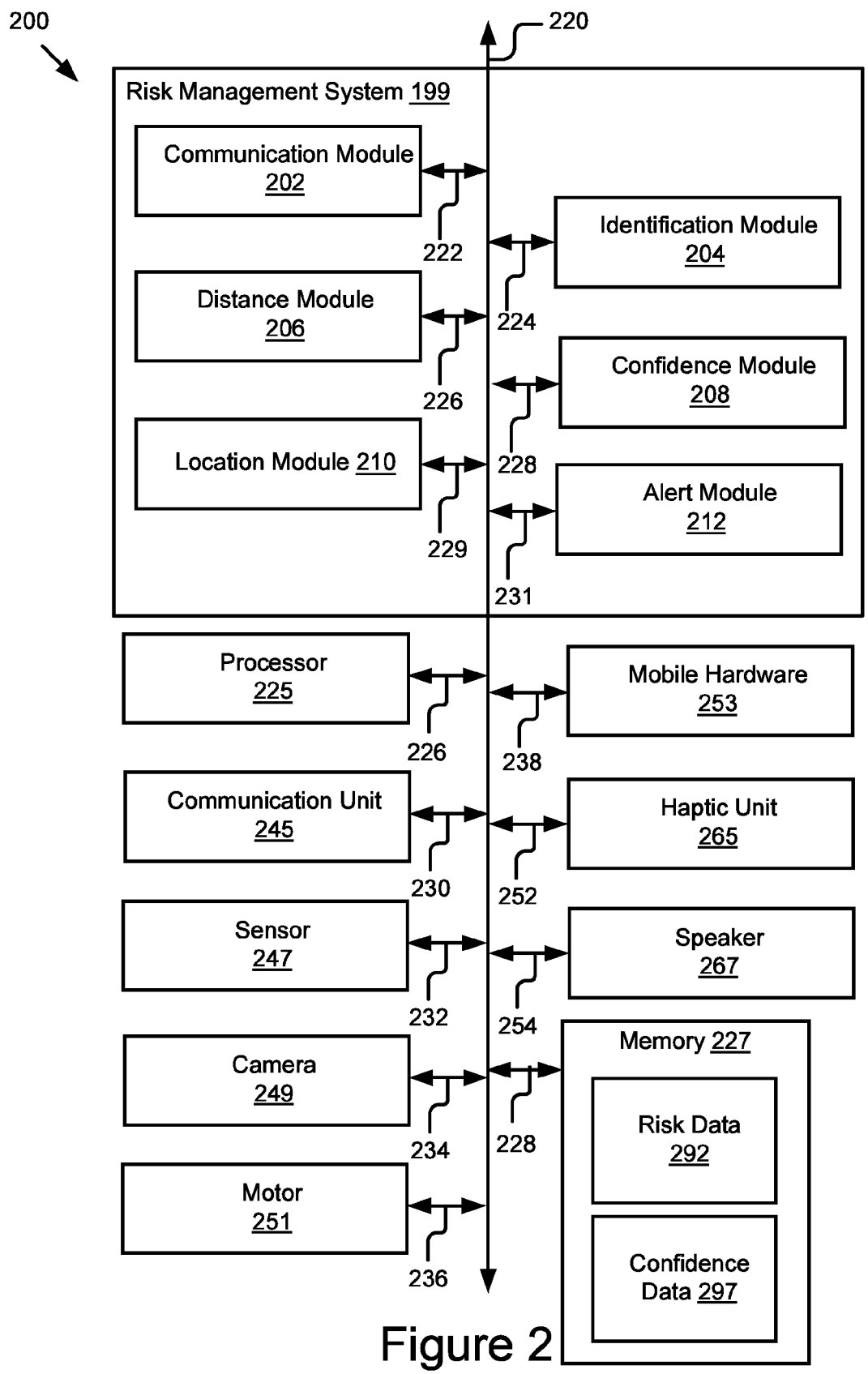
FIG. 2 is a block diagram illustrating an example risk management system.

Referring now to FIG. 2, an example of the risk management system 199 is shown in more detail. FIG. 2 is a block diagram of a system 200. The system 200 may be the robot 190 or the server 107 in the system 100 illustrated in FIG. 1. The system 200 includes the risk management system 199, a processor 225, a communication unit 245, a sensor 247, a camera 249, a motor 251, mobile hardware 253, a haptic unit 265, a speaker 267, and a memory 227, according to some examples. The components of the system 200 are communicatively coupled by a bus 220.

The processor 225 includes an arithmetic logic unit, a microprocessor, a general-purpose controller, or some other processor array to perform computations and provide electronic display signals to a display device. The processor 225 is coupled to the bus 220 for communication with the other components via a signal line 226. The processor 225 processes data signals and may include various computing architectures including a complex instruction set computer (CISC) architecture, a reduced instruction set computer (RISC) architecture, or an architecture implementing a combination of instruction sets. Although FIG. 2 includes a single processor 225, multiple processors 225 may be included. Other processors, operating systems, sensors, displays, and physical configurations may be possible.

The memory 227 stores instructions or data that may be executed by the processor 225. The memory 227 is coupled to the bus 220 for communication with the other components via a signal line 228. The instructions or data may include code for performing the techniques described herein. The memory 227 may be a dynamic random access memory (DRAM) device, a static random access memory (SRAM) device, flash memory, or some other memory device. In some embodiments, the memory 227 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

As illustrated in FIG. 2, the memory 227 stores risk data 292 and confidence data 297. The memory 227 may also store other data for providing the functionality described herein.

The risk data 292 may include, but are not limited to, data describing risk factors, such as the type of risk (drop, fixed obstacle, or mobile object), the distance between the user and the risk, and in the case of a mobile object the speed of the mobile object, the user's path, and a score assigned to each point of interest along the user's path. The risk data 292 may also include a predetermined threshold distance that is used to compare against the distance between the user and the risk to determine whether to move the robot to a new location between the user and the risk. In some embodiments, the risk data 292 is used to determine different gradations of danger. For example, the risk data 292 is divided into low-risk and high-risk danger areas based on the distance between the user and the risk.

The confidence data 297 may include, but are not limited to, data describing confidence regarding the level of danger of the risk. For example, where the distance between the user and the risk is below a predetermined threshold, the confidence is higher than if the distance is above the predetermined threshold. In some embodiments, the confidence data 297 includes a predetermined threshold for confidence that is used to determine whether the robot should be moved to a new location.

The communication unit 245 transmits and receives data to and from at least one of the server 107 and the robot 190 in the system 100. The communication unit 245 is coupled to the bus 220 via a signal line 230. In some embodiments, the communication unit 245 includes a port for direct physical connection to the network 105 or to another communication channel. For example, the communication unit 245 includes a USB, SD, CAT-5, or similar port for wired communication with other entities in the system 100. In some embodiments, the communication unit 245 includes a wireless transceiver for exchanging data with other entities in the system 100 or other communication channels using one or more wireless communication methods, including IEEE 802.11, IEEE 802.16, Bluetooth®, or another suitable wireless communication method.

In some embodiments, the communication unit 245 includes a cellular communications transceiver for sending and receiving data over a cellular communications network including via short messaging service (SMS), multimedia messaging service (MMS), hypertext transfer protocol (HTTP), direct data connection, WAP, e-mail, or another suitable type of electronic communication. In some embodiments, the communication unit 245 includes a wired port and a wireless transceiver. The communication unit 245 also provides other conventional connections to the network 105 for distribution of files or media objects using standard network protocols including TCP/IP, HTTP, HTTPS, and SMTP, etc.

In the illustrated implementation shown in FIG. 2, the risk management system 199 includes a communication module 202, an identification module 204, a distance module 206, a confidence module 208, a location module 210, and an alert module 212. These modules of the risk management system 199 are communicatively coupled to each other via the bus 220.

In some embodiments, modules of the risk management system 199 can be stored in a single server or device. In some other embodiments, modules of the risk management system 199 can be distributed and stored across multiple servers or devices. Furthermore, the separation of various components, modules, and servers in the embodiments described herein should not be understood as requiring such separation in all embodiments. In some embodiments, the described components, modules, devices, or servers can generally be integrated together in a single component, module, device, or server.

The sensor 247 is any device that senses physical changes. The sensor 247 is coupled to the bus 220 via signal line 232. In one embodiment, the sensor 247 is a motion detector. For example, the sensor 247 is a gyroscope that measures orientation of the robot 190. In another example, the sensor 247 is an accelerometer that is used to measure acceleration of the robot 190. In yet another example, the sensor 247 includes location detection, such as a global positioning system (GPS), location detection through triangulation via a wireless network, etc. In some embodiments, the sensor 247 transmits the location information to the identification module 204 and the distance module 206. In other embodiments, the sensor 247 stores the location information as part of the risk data 292 in the memory 227.

In some embodiments, the sensor 247 may include a depth sensor. In some embodiments, the depth sensor determines depth using structured light, such as a speckle pattern of infrared laser light. In another embodiment, the depth sensor determines depth using time-of-flight technology that determines depth based on the time it takes a light signal to travel between the camera and an object. The depth sensor may be used to identify drops and the dimensions of the drops including their depth. In some embodiments, the sensor 247 transmits the depth information to the identification module 204 and the distance module 206. In other embodiments, the sensor 247 stores the depth information as part of the risk data 292 in the memory 227.

The camera 249 is a physical device for capturing images that is coupled to the bus 220 via signal line 234. In one embodiment, the camera 249 captures electronic images. The camera 249 includes an image sensor, such as a charge-coupled device (CCD) or a complementary metal-oxide semiconductor (CMOS) for converting an optical image to electrical signals. In one embodiment, the camera 249 sends the electrical signals to the identification module 204 via the communication module 202 for identification of points of interest. In another embodiment, the camera 249 stores the electrical signals in the memory 227 as part of the risk data 292.

In embodiments where the system 200 is the robot 190, the system 200 includes the motor 251 and the mobile hardware 253. The motor 251 is coupled to the bus 220 via signal line 236. The mobile hardware 253 is coupled to the bus 220 via signal line 238. The mobile hardware 253 includes hardware for moving the robot 190, such as wheels. The motor 251 includes hardware for powering the mobile hardware 253. The motor 251 and the mobile hardware 253 are used to move the robot 190. For example, the confidence module 208 instructs the motor 251 to drive the mobile hardware 253 to reposition the robot 190 between the user and the risk.

The haptic unit 265 is hardware for generating vibrations that is coupled to the bus 220 via signal line 252. For example, where the system 200 is the robot 190 that the user is in physical contact with, the haptic unit 265 may vibrate in different directions to instruct the user to move in the direction of the vibration. For example, the haptic unit 265 includes four vibrating buttons that represent the four cardinal directions of north, south, east, and west. In another example, the haptic unit 265 includes eight vibrating buttons for more precise direction indicators. The haptic unit 265 receives instructions about vibrations and patterns from the alert module 212 via the communication module 202.

The speaker 267 is hardware for generating audible alerts that is coupled to the bus 220 via signal line 254. For example, where the system 200 is a robot 190, the speaker 267 receives instructions from the alert module 212 via the communication unit 202 to instruct the user to move in a particular direction, stop moving because of an imminent danger, etc.

In some embodiments, each of the modules 202, 204, 206, 208, 210, and 212 in the risk management system 199 can be a set of instructions executable by the processor 225 to provide the functionality described below. In some other embodiments, each of the modules 202, 204, 206, 208, 210, and 212 can be stored in the memory 227 and can be accessible and executable by the processor 225 of the system. Each of the modules 202, 204, 206, 208, 210, and 212 may be adapted for cooperation and communication with the processor 225 and other components of the system 200. In some embodiments, each of the modules 202, 204, 206, 208, 210, and 212 may be adapted to function as one or more thin clients that are stored and executed by a processor of the system 200.

The communication module 202 can be software including routines for handling communications between the risk management system 199 and other components of the system 200. The communication module 202 may be communicatively coupled to the bus 220 via signal line 222. The communication module 202 sends and receives data, via the communication unit 245, to and from one or more of the server 107 and the robots 190. For example, the communication module 202 receives, via the communication unit 245, a determination from the risk management system 199 on the server 107 that the robot 190 should move to a new location.

In some embodiments, the communication module 202 receives data from components of the risk management system 199 and stores the data in the memory 227. In some embodiments, the communication module 202 retrieves data the memory 227 and sends the data to one or more components of the risk management system 199. In some embodiments, the communication module 202 may handle communications between components of the risk management system 199. For example, the communication module 202 receives data from one module and sends the data to another module.

The identification module 204 can be software including routines for identifying a point of interest. The identification module 204 may be communicatively coupled to the bus 220 via signal line 224.

In some embodiments, the identification module 204 receives images from the camera 249 via the communication module 202. The identification module 204 identifies the location of the user from the images and points of interest within proximity to the user. For example, the identification module 204 identifies a fixed obstacle, such as a road, or a mobile object, such as a person. The identification module 204 may receive information about a drop from the sensor 247 via the communication unit 202. For example, the identification module 204 receives raw information about the terrain from the sensor 247 and identifies a drop based on the data. In some embodiments, the identification module 204 instructs the motor 251 to power the mobile hardware 253 to change position, and instructs the camera 249 to take additional pictures to obtain additional information about a point of interest.

The distance module 206 can be software including routines for estimating a degree of risk based on risk factors, determining a distance between the user and a point of interest, and determining whether the distance exceeds a predetermined threshold. The distance module 206 may be communicatively coupled to the bus 220 via signal line 226.

The distance module 206 receives the location of the user and points of interest from the identification module 204 via the communication module 202. The distance module 206 determines risk factors including a distance between the user and the point of interest. For example, the distance module 206 determines the distance between the user and a person that is part of a crowd.

The distance module 206 retrieves the risk data 292 including a predetermined threshold and determines whether the distance between the user and the point of interest meets the threshold. If the distance meets the threshold, the location module 210 determines where the robot 190 should be moved to mitigate risk to the user. For example, the location module 210 determines that the robot 190 should move to particular coordinates to be positioned between the risk and the user. The location may be in front of, in back of, or to the side of the user. If the distance is below the threshold, in one embodiment, the distance module 206 transmits the distance and any other risk data 292 to the confidence module 208. In another embodiment, the distance module 206 stores the risk data 292 in the memory.

Where the point of interest is a mobile object, in some embodiments, the distance module 206 determines risk factors relating to the mobile object. For example, the distance module 206 estimates the path of the user and the path of the mobile object to determine whether there will be a potential collision in the future if both the user and the mobile object continue on the same paths. In some embodiments, the distance module 206 also calculates the user's adherence to the path and determines multiple distances between the user's different paths and the point of interest. For example, if the user was walking in a zigzag pattern, the distance module 206 might determine that the user is within the threshold for distance at certain points in the zigzag pattern. In another embodiment, the distance module 206 recomputes the path if the user strays within a distance from the path. For example, if the user was walking in a straight line, and then deviates by walking diagonally to the straight line, the distance module 206 determines that the user is walking a new path once the user is five feet away from the previous path. Persons of ordinary skill in the art will recognize that other ways of calculating a deviation from the path are possible. The distance module 206 transmits this risk data 292 to the confidence module 208 or saves the risk data in the memory 227.

In some embodiments, the predetermined threshold for distance depends on the type of point of interest. For example, because people in crowds can quickly change position and become a danger or make the user nervous, in one embodiment the distance module 206 applies an eight-foot predetermined threshold for distance to mobile objects and a five-foot predetermined threshold for distance to drops and fixed obstacles.

In some embodiments, the distance module 206 determines a path for the user, identifies points of interest along the path, and assigns a score to the points of interest based on the user's path. The score may be based on a distance between the user's path and the point of interest, and a predetermined threshold for distance that depends on the type of point of interest. For example, the path includes a mobile object and a drop. The distance module 206 determines that the user will be four feet from the mobile object, which has a predetermined threshold of two feet. The distance module 206 divides the distance by the threshold to assign a score of 2. The distance module 206 determines that the drop will be two feet from the user's path and the predetermined threshold is four feet. The distance module 206 divides the distance by the threshold to assign a score of 0.5. Other techniques for assigning a score are possible.

The confidence module 208 can be software including routines for determining a confidence indicating a likelihood of an actual risk and whether the confidence meets a predetermined threshold. The confidence module 208 may be communicatively coupled to the bus 220 via signal line 228.

In one embodiment, the confidence module 208 receives the risk data 292 from the distance module 206 via the communication module 202. In another embodiment, the confidence module 208 retrieves the risk data 292 from the memory 227. The confidence module 208 uses the risk data 292 including a distance between the user and the point of interest to calculate an amount of risk associated with the point of interest. For example, the confidence module 208 determines that there is an 80% chance that the user will collide with the point of interest. In some embodiments, the confidence module 208 determines the amount of risk as a function of time. The confidence module 208 makes use of both the user's trajectory and the trajectory of a mobile object to determine the risk. For example, the confidence module 208 determines that there is a 60% chance that the user will collide with the point of interest in the next five seconds, an 80% chance that the user will collide with the point of interest in the next 10 seconds, etc.

In some embodiments the confidence module 208 modifies the confidence based on the user's adherence to a path. For example, where the user deviates frequently from the path, the confidence module 208 determines a lower confidence value.

The confidence module 208 determines whether the confidence meets a predetermined threshold for confidence. If the confidence meets or exceeds a predetermined threshold, the location module 210 determines where to move the robot 190 to mitigate risk to the user and instructs the robot 190 to move to a new location. For example, the location module 210 determines that the robot 190 should move to particular coordinates to be positioned between the risk and the user. If the confidence is below the predetermined threshold, the process begins again with the identification module identifying a point of interest.

The location module 210 can be software including routines for determining where to move the robot 190 to mitigate risk to the user and for instructing the robot 190 to move to a new location. The location module 210 may be communicatively coupled to the bus 220 via signal line 229.

The location module 210 may receive the risk data 292 from the distance module 206 via the communication module 202, the confidence data 297 from the confidence module 208 via the communication module 202, or the location module 210 may retrieve the risk data 292 and/or the confidence data 297 from the memory 227. If the distance between the user and a point of interest meets or exceeds a predetermined threshold for distance, the distance module 206 instructs the location module 210 to determine where to move the robot 190 to mitigate risk to the user. For example, where the point of interest is a drop located five feet from the user, the location module 210 instructs the motor 251 to power the mobile hardware 253 to reposition the robot 190 about 2.5 feet from the drop in front of the user.

If the distance between the user and a point of interest is less than the predetermined threshold for distance and the confidence meets or exceeds the predetermined threshold for confidence, the confidence module 208 instructs location module 210 to determine where to move the robot 190 to mitigate risk to the user. In some embodiments, the location module 210 determines when to reposition the robot 190 based on when the confidence meets or exceeds the predetermined threshold for confidence. For example, the confidence module 208 determines that there is a 50% chance that the user will collide with a person in a crowd in the next 10 seconds, but if the user continues to move toward the crowd the confidence will increase to 80% in the next 12 seconds. As a result, the location module 210 instructs the robot 190 to move to a new location at the 12-second mark.

The alert module 212 can be software including routines for determining whether to warn the user and, if so, providing a warning for the user. The alert module 212 may be communicatively coupled to the bus 220 via a signal line 231.

In one embodiment, the alert module 212 determines whether to warn the user in response to the robot 190 repositioning itself. For example, the alert module 212 warns the user that the robot 190 is now between the user and the point of interest and that the user should change direction. In another embodiment, the alert module 212 determines whether to warn the user based on the closeness of the point of interest. For example, the alert module 212 warns the user that there is a drop less than four feet from the user.

The alert module 212 provides an auditory or tactile warning to the user. The auditory warning includes, for example, instructions to activate the speaker 267 on the robot 190 to issue a warning about the position of the robot 190. The auditory warning could be a sound, such as a chime, or a verbal warning. The tactile warning includes instructions to the haptic unit 265 on the robot 190 to vibrate to indicate a directional change that the user should take. In embodiments where the user is not in physical contact with the robot 190, the alert module 212 may transmit the tactile warning to a different device via the communication unit 245. For example, the user may be wearing a belt with eight buttons that vibrate in eight different directions. In another example, the user holds a walking stick with four buttons on the handle that vibrate to indicate direction. For example, the first button represents north, the second button represents east, the third button represents south, and the fourth button represents west.

Example Scenario

Figure 3:
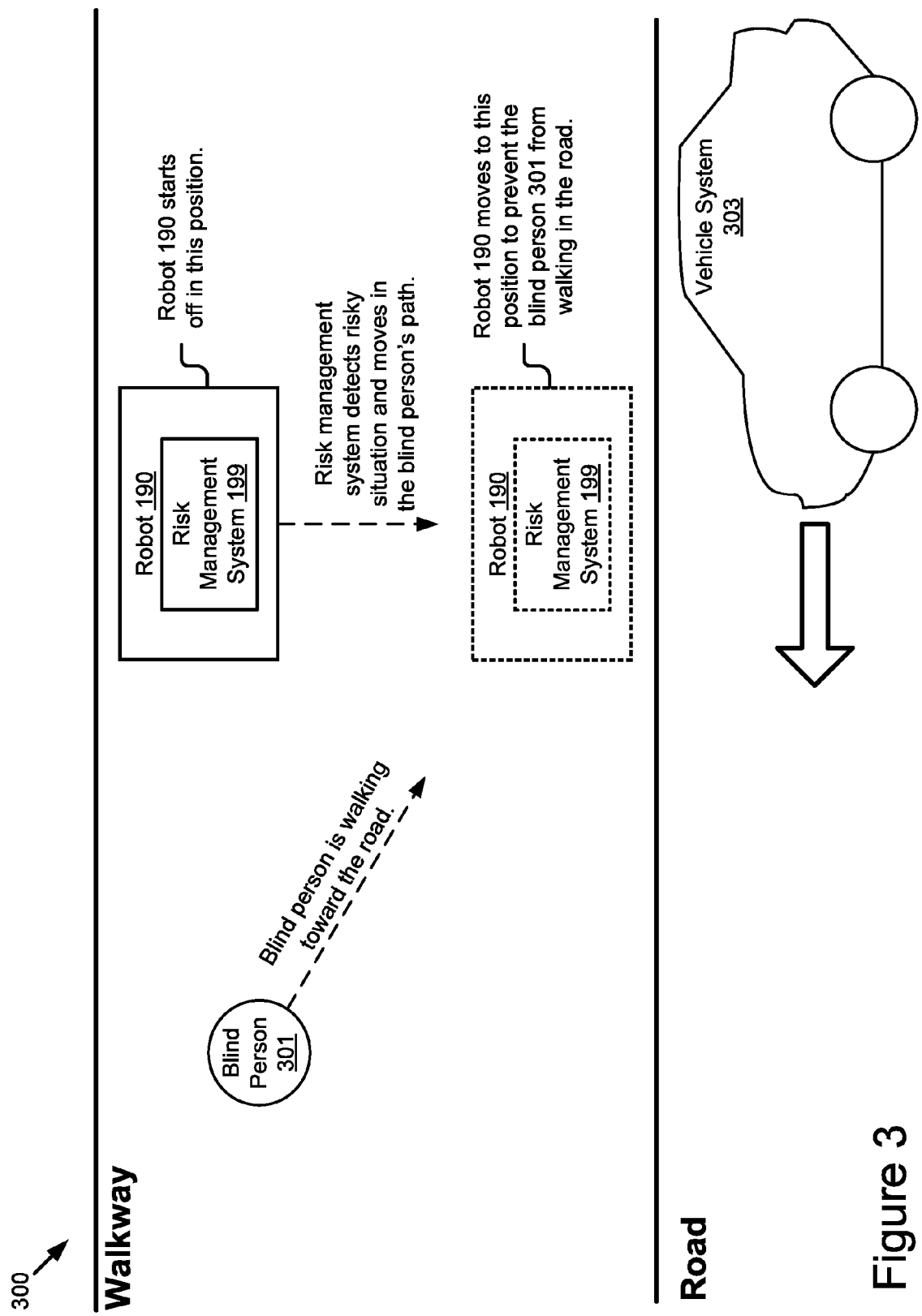
FIG. 3 is a block diagram illustrating an example scenario where the robot prevents risk to the user.

Referring now to FIG. 3, an example scenario 300 is illustrated. In this example, the visually impaired user is a blind person 301. The blind person 301 is walking southeast towards the road that includes a vehicle system 303. The trajectory of the user is such that the user will collide with the vehicle system 303 on the road. The robot 190 is positioned northeast of the user. The risk management system 199 stored on the robot 190 determines that the vehicle system 303 is a mobile object that could harm the user. The risk management system 199 instructs the robot 190 to move to a new position to prevent the blind person 301 from walking into the road. In some embodiments, the robot 190 warns the blind person 301 either by emitting an auditory warning or transmitting haptic feedback to change directions. Even if the blind person 301 ignored the warning, the blind person 301 would collide with the robot 190 before walking into the road. As a result, the robot 190 protects the blind person 301 from harm.

Example Methods

Figure 4A:
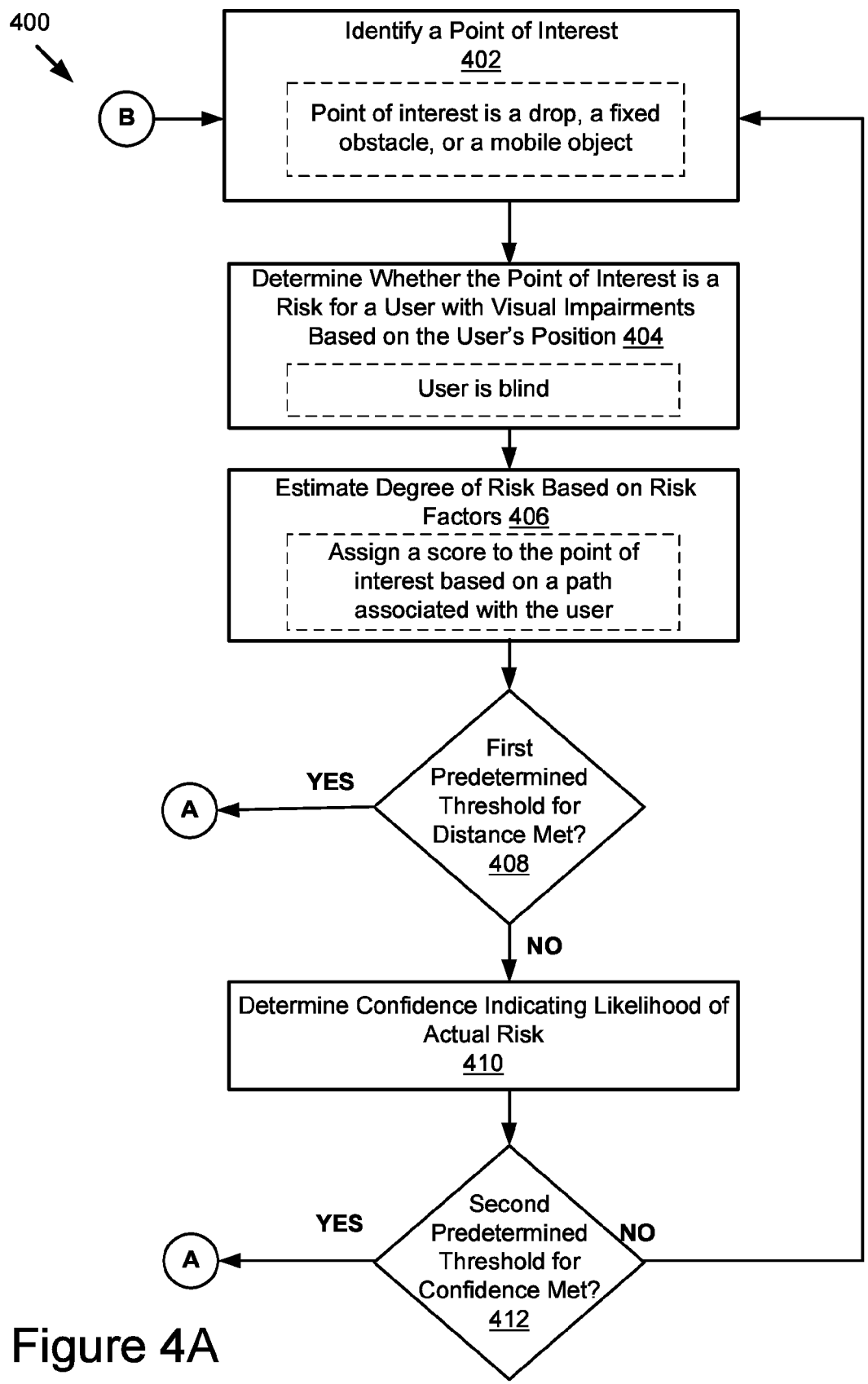
FIGS. 4A-4B are a flowchart of an example method for using a robot to prevent risk to a user.
Figure 4B:
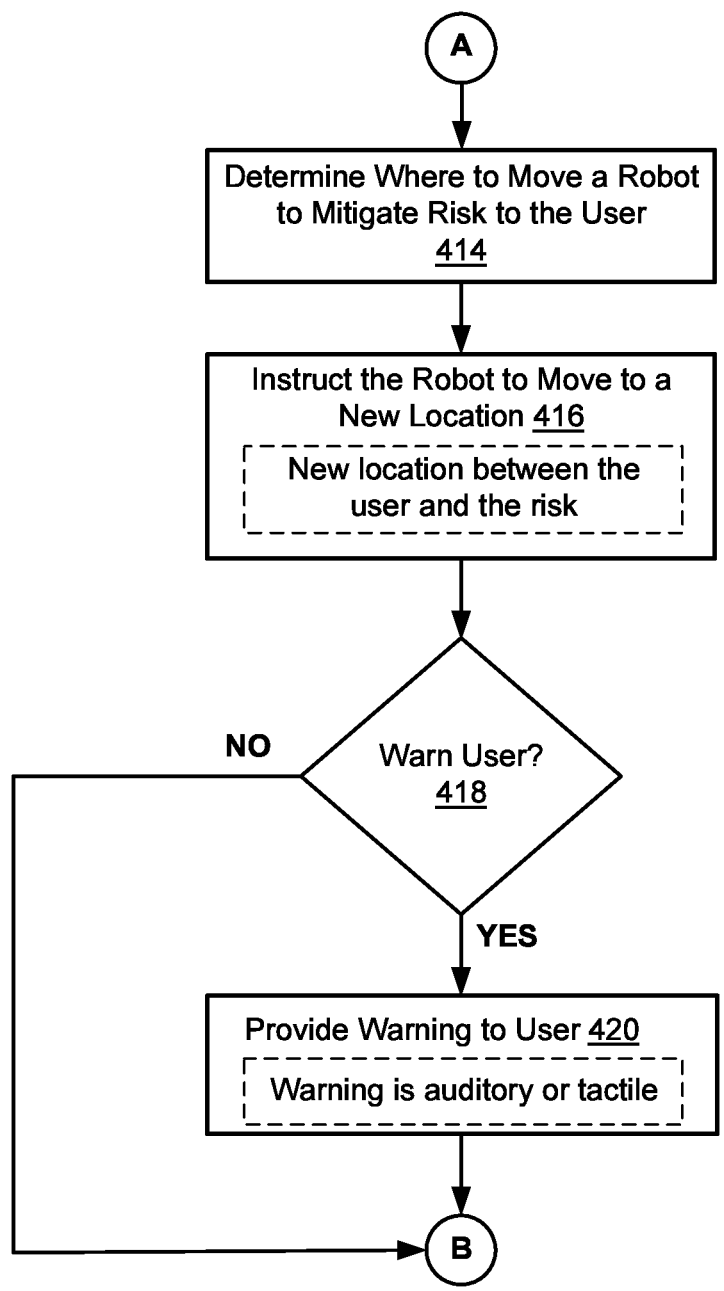

Referring now to FIGS. 4A-4B, an example of a method 400 for using a robot to prevent risk to the user is described. In some embodiments, one or more processor-based computing devices are programmed to perform one or more of the steps of the method 400. The steps of the method 400 may be performed in any order. In some embodiments, the method 400 may be performed by modules of the risk management system 199 stored on the server 107 or the robot 190. For example, the risk management system 199 may include an identification module 204, a distance module 206, a confidence module 208, a location module 210, and an alert module 212.

The identification module 204 identifies 402 a point of interest. The point of interest may be, for example, a drop, a fixed obstacle, or a mobile object. The distance module 206 determines 404 whether the point of interest is a risk for the user with visual impairments based on the user's position. In some embodiments, the user is blind.

The distance module 206 estimates 406 a degree of risk based on risk factors. For example, the distance module determines a path for the user and assigns a score to the point of interest based on the path associated with the user. The distance module 206 determines 408 whether a first predetermined threshold for distance was met. If the first predetermined threshold was met, the method proceeds to step 414. If the distance between the user and the point of interest is below the first predetermined threshold for distance, the method proceeds to step 414.

In some embodiments the distance module 206 transmits the risk data 292 to the confidence module 208. In other embodiments, the confidence module 208 retrieves the risk data 292 from the memory 227. The confidence module 208 determines 410 confidence indicating a likelihood of actual risk. For example, the confidence module 208 determines that there is an 80% chance that the user will collide with a stationary object if the user continues on the same path. The confidence module 208 determines 412 whether a second predetermined threshold for confidence is met. If the second predetermined threshold for confidence is not met, the method begins again at step 402 by identifying a point of interest. If the second predetermined threshold for confidence is met, the method proceeds to step 414.

The location module 210 determines 414 where to move the robot 190 to mitigate risk to the user. The location module 210 instructs 416 the robot 190 to move to a new location. For example, the new location is between the user and the risk so that the user will collide with the robot 190 and not stumble into a ditch. In embodiments where the risk management system 199 is on the server 107, the communication unit 245 sends the instructions to the robot 190. In embodiments where the risk management system 199 is on the robot 190, the location module 210 transmits the instructions to the motor 251, which powers the mobile hardware 253 to move to the new position.

The alert module 212 determines 418 whether to warn the user. For example, the alert module 212 warns the user to change paths. In some embodiments, the alert module 212 uses different warnings depending on the distance between the user and the robot 190. For example, the first warning is quieter than the second warning. If the alert module 212 determines that the user should not be warned, the method starts again at step 402 by identifying a point of interest. If the alert module 212 determines to warn the user, the alert module 212 provides 420 the warning to the user. The warning may be auditory or tactile. For example, the alert module 212 transmits instructions to a belt worn by the user to vibrate in the direction that the user should move to avoid colliding with the robot.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the embodiments can be described above primarily with reference to user interfaces and particular hardware. However, the embodiments can apply to any type of computing device that can receive data and commands, and any peripheral devices providing services.

Reference in the specification to "some embodiments" or "some instances" means that a particular feature, structure, or characteristic described in connection with the embodiments or instances can be included in at least one implementation of the description. The appearances of the phrase "in some embodiments" in various places in the specification are not necessarily all referring to the same embodiments.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The embodiments of the specification can also relate to an apparatus for performing the operations herein. This apparatus may be specially constructed for the required purposes, or it may include a general-purpose computer selectively activated or reconfigured by a computer program stored in the computer. Such a computer program may be stored in a computer-readable storage medium, including, but is not limited to, any type of tangible, non-transitory disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory, or any type of media suitable for storing electronic instructions, each coupled to a computer system bus. In some embodiments, the apparatus may include a tangible, non-transitory memory storing executable instructions executable by one or more processors to perform or control performance of operations corresponding to one or more of the method 400 steps described above for FIGS. 4A and 4B.

The specification can take the form of some entirely hardware embodiments, some entirely software embodiments, or some embodiments containing both hardware and software elements. In some preferred embodiments, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A data processing system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including, but not limited, to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem, and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the embodiments of the specification has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions, or formats. Furthermore, as will be apparent to one of ordinary skill in the relevant art, the modules, routines, features, attributes, methodologies, and other aspects of the disclosure can be implemented as software, hardware, firmware, or any combination of the three. Also, wherever a component, an example of which is a module, of the specification is implemented as software, the component can be implemented as a standalone program, as part of a larger program, as a plurality of separate programs, as a statically or dynamically linked library, as a kernel-loadable module, as a device driver, or in every and any other way known now or in the future to those of ordinary skill in the art of computer programming. Additionally, the disclosure is in no way limited to implementation in any specific programming language, or for any specific operating system or environment. Accordingly, the disclosure is intended to be illustrative, but not limiting, of the scope of the specification, which is set forth in the following claims.

What is claimed is:

1. A method for a robot, comprising:
   identifying, with one or more processors, a point of interest;
   determining whether the point of interest is a risk for a user with visual impairments based on the user's position;
   responsive to a first predetermined threshold for distance failing to be met, determining a confidence factor that indicates a likelihood of actual risk;
   responsive to a second predetermined threshold for confidence being met, determining where to move the robot to mitigate risk to the user; and
   instructing the robot to move to a new location.

2. The method of claim 1, further comprising estimating a degree of risk based on risk factors by assigning a score to the point of interest based on a path associated with the user.

3. The method of claim 1, further comprising:
   determining whether to warn the user; and
   responsive to determining to warn the user, providing a warning to the user.

4. The method of claim 3, wherein the warning is at least one of an auditory warning and a tactile warning.

5. The method of claim 3, wherein the warning is a tactile warning and further comprising transmitting the warning to a walking stick that provides the user with haptic feedback.

6. The method of claim 1, further comprising:
   determining whether to warn the user; and
   responsive to determining not to warn the user, identifying a second point of interest.

7. The method of claim 1, further comprising responsive to a second predetermined threshold for confidence failing to be met, identifying a second point of interest.

8. The method of claim 1, wherein the point of interest comprises at least one of a drop, a fixed obstacle, and a mobile object.

9. A computer program product for a robot comprising a non-transitory computer-usable medium including a computer-readable program, wherein the computer-readable program when executed on a computer causes the computer to:
   identify a point of interest;
   determine whether the point of interest is a risk for a user with visual impairments based on the user's position;
   responsive to a first predetermined threshold for distance failing to be met, determining a confidence factor that indicates a likelihood of actual risk;
   responsive to a second predetermined threshold for confidence being met, determining where to move the robot to mitigate risk to the user; and
   instruct the robot to move to a new location.

10. The computer program product of claim 9, wherein the computer-readable program is further configured to estimate a degree of risk based on risk factors by assigning a score to the point of interest based on a path associated with the user.

11. The computer program product of claim 9, wherein the computer-readable program is further configured to:
    determining whether to warn the user; and
    responsive to determining to warn the user, providing a warning to the user.

12. The computer program product of claim 11, wherein the warning is at least one of an auditory warning and a tactile warning.

13. The computer program product of claim 11, wherein the warning is a tactile warning and further comprising transmitting the warning to a walking stick that provides the user with haptic feedback.

14. A system for a robot, comprising:
a processor; and
a memory storing instructions that, when executed, cause the system to:
identify a point of interest;
determine whether the point of interest is a risk for a user with visual impairments based on the user's position;
responsive to a first predetermined threshold for distance failing to be met, determine a confidence factor that indicates a likelihood of actual risk;
responsive to a second predetermined threshold for confidence being met, determine where to move the robot to mitigate risk to the user; and
instruct the robot to move to a new location.

15. The system of claim 14, wherein the memory is further configured to estimate a degree of risk based on risk factors by assigning a score to the point of interest based on a path associated with the user.

16. The system of claim 15, wherein the memory is further configured to:
determining whether to warn the user; and
responsive to determining to warn the user, providing a warning to the user.

17. The system of claim 16, wherein the warning is at least one of an auditory warning and a tactile warning.

18. The system of claim 16, wherein the warning is a tactile warning and further comprising transmitting the warning to a walking stick that provides the user with haptic feedback.

19. A method comprising:
identifying, with one or more processors, a first point of interest;
determining whether the first point of interest is a risk for a user with visual impairments based on the user's position;
responsive to a first predetermined threshold for distance failing to be met for the first point of interest, determining a confidence factor that indicates a likelihood of actual risk;
responsive to a second predetermined threshold for confidence failing to be met, identifying a second point of interest;
determining whether the second point of interest is a risk for the user with visual impairments based on the user's position;
responsive to the first predetermined threshold for distance being met for the second point of interest, determining where to move a robot to mitigate the risk to the user; and
instructing the robot to move to a new location.

20. A computer program product comprising a non-transitory computer-usable medium including a computer-readable program, wherein the computer-readable program when executed on a computer causes the computer to:
identify a first point of interest;
determine whether the first point of interest is a risk for a user with visual impairments based on the user's position;
responsive to a first predetermined threshold for distance failing to be met for the first point of interest, determine a confidence factor that indicates a likelihood of actual risk;
responsive to a second predetermined threshold for confidence failing to be met, identify a second point of interest;
determine whether the second point of interest is a risk for the user with visual impairments based on the user's position;
responsive to the first predetermined threshold for distance being met for the second point of interest, determine where to move a robot to mitigate the risk to the user; and
instruct the robot to move to a new location.

21. A system comprising:
a processor; and
a memory storing instructions that, when executed, cause the system to:
identify a first point of interest;
determine whether the first point of interest is a risk for a user with visual impairments based on the user's position;
responsive to a first predetermined threshold for distance failing to be met for the first point of interest, determine a confidence factor that indicates a likelihood of actual risk;
responsive to a second predetermined threshold for confidence failing to be met, identify a second point of interest;
determine whether the second point of interest is a risk for the user with visual impairments based on the user's position;
responsive to the first predetermined threshold for distance being met for the second point of interest, determine where to move a robot to mitigate the risk to the user; and
instruct the robot to move to a new location.

* * * * *